United States Patent [19]

Abraham et al.

[11] Patent Number: 4,669,458

[45] Date of Patent: Jun. 2, 1987

[54] I.V. HOLDER

[75] Inventors: William W. Abraham, New Hartford; Edward H. Majka, Utica, both of N.Y.

[73] Assignee: ConMed Inc., Utica, N.Y.

[21] Appl. No.: 381,755

[22] Filed: May 25, 1982

Related U.S. Application Data

[63] Continuation of Ser. No. 128,462, Mar. 10, 1980, abandoned.

[51] Int. Cl.⁴ .............................................. A61M 5/00
[52] U.S. Cl. ........................... 128/133; 128/DIG. 26; 604/180
[58] Field of Search .......... 128/DIG. 26, 133, 214 R, 128/214.4; 604/180

[56] References Cited

U.S. PATENT DOCUMENTS

| | | | |
|---|---|---|---|
| 3,677,250 | 7/1972 | Thomas | 128/133 X |
| 3,782,377 | 1/1974 | Rychlik | 128/DIG. 26 X |
| 3,782,378 | 1/1974 | Page | 128/133 |
| 3,900,026 | 8/1975 | Wagner | 128/DIG. 26 X |
| 3,973,565 | 8/1976 | Steer | 128/214.4 |
| 4,059,105 | 11/1977 | Cutruzzula et al. | 128/DIG. 26 X |

Primary Examiner—Mickey Yu
Attorney, Agent, or Firm—Larson and Taylor

[57] ABSTRACT

A holder for securing and protecting an intravenous injection needle when the needle is inserted in the body of a patient is disclosed. The holder includes a flat base having an adhesive bottom with an aperture located in the middle of the base. A clear plastic window, having an adhesive bottom, is placed over the aperture on the base. When the needle is inserted in the body, the base is placed over the needle so that the insertion site lies in the middle of the aperture. The base securely holds the needle in place, and the clear window covers and protects the needle while allowing the needle insertion site to be observed. The window can be partially peeled back to provide access to the needle, and if desired the window may be completely peeled off and replaced. A see through gauze pad to which an antibiotic salve can be applied is also disclosed. This gauze pad is removably placed underneath the clear window in the aperture. In order to prevent any further stress on the needle, a fully adhesive strip is placed across the tube leading to the needle. Adjacent to this adhesive strip is a second adhesive strip with a central non-adhesive portion. The first adhesive strip holds the tube securely in place, while the second adhesive strip holds the tube to the body but allows the tube to slide beneath the strip.

1 Claim, 6 Drawing Figures

I.V. HOLDER

This is a continuation of the application Ser. No. 128,462, filed Mar. 10, 1980, now abandoned.

FIELD OF THE INVENTION

This invention relates generally to holders for securing and protecting an intravenous injection needle and more particularly to a holder having a window through which the insertion site may be viewed and the insertion site may be exposed by peeling back the window.

BACKGROUND OF THE INVENTION

In the use of a needle or catheter which is inserted intravenously into a patient, it is common to secure the needle and tubing to the patient by taping. In order to maintain the sterility of the needle, a sterile gauze pad is placed over the needle and taped to the body. Not only is the tearing of the adhesive strips and positioning of the gauze time consuming, but the needle or tubing can easily come loose unless the adhesive strips are properly and securely placed. In addition, if it is desired to inspect the insertion site or apply an antibiotic, the adhesive strips must be lifted and then carefully replaced. Failure to inspect the insertion site can result in undetected infiltration.

A number of devices in the prior art have been disclosed which hold the needle down and allow observation of the insertion site. For example, in U.S. Pat. No. 3,900,026 to Wagner and No. 3,782,377 to Rychlik, a transparent dome is adhesively held over the needle insertion site. Another patent disclosing a transparent window over the insertion site is U.S. Pat. No. 3,782,378 to Page. In this patent, the flexible transparent cover is held in place by an elastic band. Besides a transparent window, it has also been suggested that an easily raised covering be used to allow inspection of the insertion site whenever desired. In U.S. Pat. No. 4,059,105 to Cutruzzula et al, a first layer having an aperture is adhesively attached over the needle and insertion site. A second, wider portion is then foldable over this first portion and it too is adhesively held to the body. When desired, the second portion is peeled back to expose the aperture in the first portion for inspection of the insertion site. Instead of viewing the insertion site itself, it has also been suggested that a site near the insertion site be observed instead. Thus, in U.S. Pat. No. 3,973,565 to Steer, an adhesive covering for holding a needle down has an aperture which is located near the insertion site.

There are a number of disadvantages to each of the prior art systems. Where the insertion site is observable in the prior art, it is generally not easily accessible. On the other hand, where the insertion site is accessible as in the device disclosed in the Cutruzzula et al patent, it is not observable at all times. In addition, the constant peeling back of the upper layer in such a device to observe the insertion site would irritate the skin to which the upper layer is adhesively secured.

SUMMARY OF THE INVENTION

In accordance with the present invention, a holder is provided for securing and shielding an intravenous injection needle when the needle is inserted in the body of a patient. The present invention allows for the needle to be quickly and easily covered and secured immediately after it is inserted. In addition, the present invention allows the insertion site to be readily observed at all times and to be easily accessed whenever desired. According to a preferred embodiment, the invention comprises a flat adhesive base with an aperture located therein and a clear plastic window with an adhesive bottom lying over the aperture which can be easily peeled back to expose the aperture. In use, a see through gauze pad can be placed in the aperture underneath the window, and adhesive strips can be used to secure the tube leading to the needle to the body in order to reduce any strain on the needle which might be caused by the tube.

Other features and advantages of the present invention are stated in or are apparent from the detailed description of a presently preferred embodiment of the invention found herein below.

DETAILED DESCRIPTION OF THE PREFERRED EMBODIMENT

Figure 1:
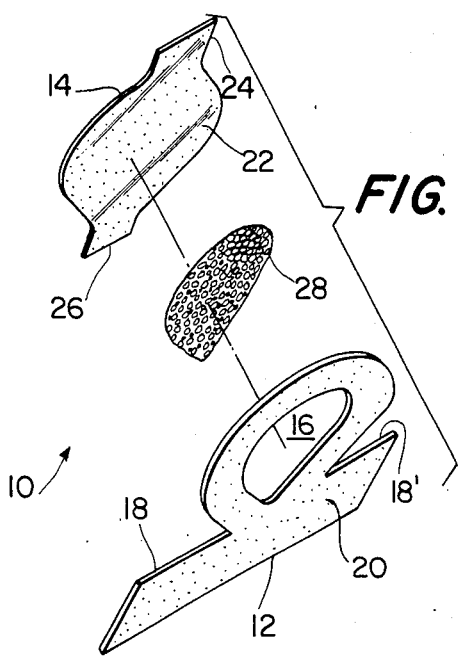
FIG. 1 is an exploded perspective view of the needle holder of the present invention.
Figure 2:
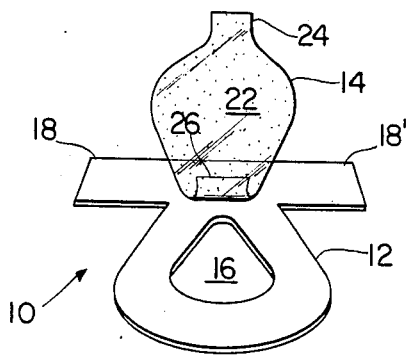
FIG. 2 is a perspective view of the needle holder of the present invention with the transparent window peeled back.

With reference now to the drawings in which like numerals represent like elements throughout the several views, a presently preferred embodiment of the present invention is depicted in FIGS. 1 and 2 and comprises a needle holder 10 having a flat base 12 and a clear plastic window 14. Flat base 12 is made from a suitable material, such as 1/16 inch "White Foam" crosslinked polyethlene material. Located in the middle of the flat base 12 is an aperture 16. A pair of wings 18 and 18' extend on either side of one end of flat base 12. Both flat base 12 and wings 18 and 18' have an adhesive layer 20 on their bottom portions. Clear plastic window 14 also has an adhesive layer 22 on its bottom portion for adhering window 14 to base 12. Alternatively, base 12 may have adhesive on the upper surface for the same purpose. It is also possible to use a plastic material such as Saranwrap for the window which tends to cling to a substrate without use of an adhesive. A first tab 24 extends out from window 14 slightly beyond the base 12. At the other end of window 14, a second tab 26 extends over a portion of wings 18 and 18'.

If desired, a see-through gauze pad 28 can be located in aperture 16 underneath window 14. Gauze pad 28 may be made of any suitable material, such as a loosely woven cotton fabric or a thin layer of cellular foam. Where gauze pad 28 is made from a fabric, it will adhere to adhesive layer 22 of window 14. However, where gauze pad 12 is made from certain types of cellular foam, it may not adhere to window 14 and thus is easily removable from aperture 16 when desired. Obviously, if the base 12 is provided with adhesive instead of window 14, the gauze pad will not adhere to the window. There are advantages to both arrangements. Where the gauze pad adheres to the window the I.V. site is immediately exposed when the window is removed. If the window and gauze pad are not adhered together, it is a simple matter to remove the gauze pad after the window is removed.

Figure 3:
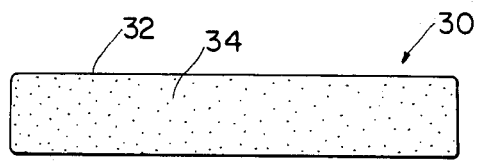
FIG. 3 is a bottom view of a first adhesive strip.
Figure 4:
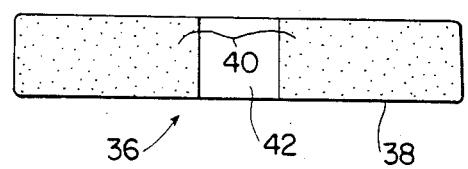
FIG. 4 is a bottom view of a second adhesive strip.

A tube holder 30 is shown in FIG. 3. Tube holder 30 is made from a strip 32 having an adhesive layer 34 applied to its bottom. A similar tube holder 36 is shown in FIG. 4 which likewise comprises a strip 38 with an adhesive layer 40 on its bottom. Tube holder 36 also has a non-adhesive area 42 which separates adhesive layer 40 into two parts. Conveniently, both tube holders 30 and 36 can be formed from one sixteenth inch "White Foam" with a suitable adhesive. The non-adhesive area 42 can be easily formed by applying adhesive layer 40 over the entire strip 38 and then using this adhesive to hold a piece of paper forming the non-adhesive area 42.

Figure 5:
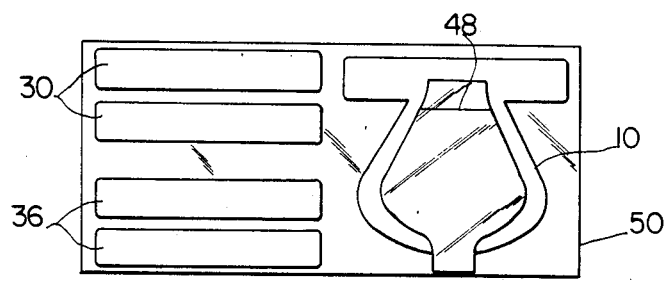
FIG. 5 is a top view of the present invention mounted on a clear plastic base from which it is transferred to the patient.

For the convenience of hospital personnel, needle holder 10 and tube holders 30 and 36 are conveniently stored adhesive layer down on a suitable clear plastic mount 50 as shown in FIG. 5. In order to keep needle holder 10 and tube holders 30 and 36 sterile, the entire assembly shown in FIG. 5 is packaged in a sterile or sterilizable pouch (not shown). While in the pouch, it is advisable to place a piece of protective paper 48 underneath clear plastic window 14 and first tab 24. In this matter second tab 26 holds clear plastic window 14 in place, and the piece of protective paper 48 prevents the rest of clear window 14 from becoming tightly adhered to flat base 12 prior to usage. At the time of usage, this piece of protective paper is easily removed and discarded.

Figure 6:
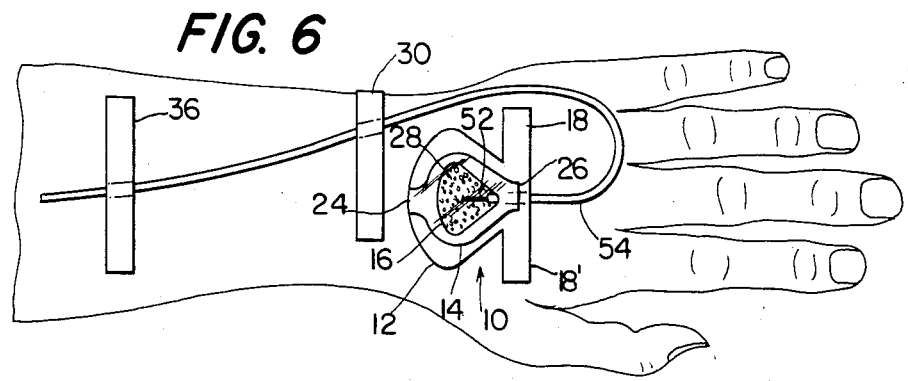
FIG. 6 is a schematic view of the present invention being used to hold a needle and tubing to the hand of a patient.

In use, needle holder 10 and tube holders 30 and 36 function in the following manner as shown in FIG. 6. Initially, clear plastic mount 50 with needle holder 10 and tube holders 30 and 36 attached is taken out of the sterilized pouch and positioned where it can be reached readily. Next, a needle 52 with an attached tube 54 is inserted into a view of the patient, for example a vein in the hand as shown in FIG. 6. Once the needle is in place, needle holder 10 is peeled off of plastic mount 50 and positioned over needle 52 such that the insertion site lies in the center of aperture 16 and the exposed portion of needle 52 extends underneath of base 12 between wings 18 and 18'. In order for needle holder 10 to hold needle 52 in place effectively, a portion of tube 54 must be secured to the patient. To accomplish this, one or more adhesive strips 30 are placed over tube 54 adjacent to needle holder 10. Tube holder 30 secures and holds tube 54 relatively immovably to the body. Adjacent to tube holder 30, one or more tube holders 36 is used to further secure tube 54 to the body. However, because of the nonadhesive layer 42 on tube holder 36, tube 54 is free to slide underneath tube holder 36. By allowing tube 54 to slide underneath tube holder 36, tube 54 can move slightly without putting strain on the needle 52 and this is more comfortable for the patient. With needle 52 and tube 54 secured in place, gauze pad 28 can be removed from aperture 16, or an antibiotic salve can be applied to gauze pad 28 which is then left in aperture 16. Finally, the piece of protective paper 48 attached to adhesive layer 22 of clear window 14 is removed and clear window 14 is pressed onto flat base 12 where it adheres. It is also possible, of course, that the protective paper may be taken off before applying the I.V. holder to the patient and before removing the unit from the carrier. In this way, the holder may be applied to the patient as a unit. With clear window 14 in place, the needle insertion site is fully shielded but is is readily seen through window 14.

If it is desired to more closely inspect the insertion site or to apply more antibiotic salve to the site, clear window 14 is easily peeled back by grasping first tab 24. When window 14 is peeled back to expose aperture 16, second tab 26 remains adhered to base 12. In this manner, after direct access to the insertion site is no longer necessary, clear window 14 is then simply lowered back to its former position where it adheres to flat base 12 again and protects the site. It would also be possible to completely remove clear window 14 and replace it with a new one if necessary.

While the shape of needle holder 10 disclosed is preferred, a variety of other shapes are also possible. For example, a butterfly shape or a star shape could also be used. In addition, a second aperture could be provided in needle holder 10 and the needle and tube could exit from the second aperture.

Furthermore, it is possible to eliminate the adhesive from a tab portion of the window to provide a means for grasping the window for removal. Alternatively the tab may be coated with adhesive and folded upon itself to prevent the adhesive from engaging the base, thus providing removal means.

It may further be desirable to provide that the needle is not directly secured to the I.V. holder. This will insure that the needle does not puncture the blood vessel. This can be achieved by eliminating the adhesive from the area of the base between wings 18 and 18' or by providing a plastic insert in this area secured to the holder which captivates the hub of the needle. If a plastic insert is used to retain the needle, this may be located above or below the I.V. needle and it may be necessary to provide a pad between the I.V. needle hub and the skin to prevent the needle hub from digging into the skin. It is further contemplated that a different type of adhesive could be used on the base in the area where the I.V. needle hub passes beneath the base. The adhesive in this area may be less agressive than the remaining adhesive so that when the bandage is removed the I.V. needle will not be forced into the skin and yet the bandage will effectively retain the needle in position by firmly gripping the skin around the insertion site.

It is possible that wings 18 and 18' having adhesive thereon could be replaced with elongated tapes having Velco on the end portions which could extend around the hand and secured together to retain the I.V. holder in place.

I claim:

1. A holder for securing and shielding a needle when the needle is inserted in the body of a patient comprising:
    a base including wings having an adhesive bottom for adhering to the body of a patient;
    a first type of adhesive on the outer end portions of said base to provide substantial adhering characteristics to the patient and a second type of adhesive between said wings where the hub of the needle is received, said second type of adhesive providing less adhering characteristics than said first type of adhesive to prevent puncturing the vein when removing the holder;
    an aperture located in said base;
    a flexible window having a bottom which reattachably adheres to said base, said window being larger than said aperture and located over said aperture on said base, said window having no portion in engagement with the body of the patient, said window including a first tab portion extending from said window such that said tab portion is easily grasped to peel back said window;

such that when the needle is inserted in the patient, said base with said window attached is placed over the needle with the needle insertion site in the center of the aperture whereby the needle insertion site is easily observable and treatable by temporarily peeling back said window.

* * * * *